(12) United States Patent
Elgort et al.

(10) Patent No.: US 8,452,376 B2
(45) Date of Patent: May 28, 2013

(54) ELECTROMAGNETIC LOCALIZATION SYSTEM

(75) Inventors: Daniel R. Elgort, New York, NY (US); Lucian R. Albu, Forest Hills, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 605 days.

(21) Appl. No.: 12/596,837

(22) PCT Filed: Apr. 22, 2008

(86) PCT No.: PCT/IB2008/051541
§ 371 (c)(1),
(2), (4) Date: Feb. 9, 2010

(87) PCT Pub. No.: WO2008/132657
PCT Pub. Date: Nov. 6, 2008

(65) Prior Publication Data
US 2010/0145192 A1    Jun. 10, 2010

Related U.S. Application Data

(60) Provisional application No. 60/914,049, filed on Apr. 26, 2007.

(51) Int. Cl.
*A61B 5/00* (2006.01)
(52) U.S. Cl.
USPC .......................................... 600/424; 600/430
(58) Field of Classification Search
USPC ................... 600/407, 430, 476–478
See application file for complete search history.

(56) References Cited

U.S. PATENT DOCUMENTS

| 5,383,467 | A | 1/1995 | Auer et al. | |
|---|---|---|---|---|
| 5,541,730 | A | 7/1996 | Chaney | |
| 6,853,457 | B2 | 2/2005 | Bjarklev et al. | |
| 7,152,608 | B2 | 12/2006 | Hunter et al. | |
| 8,032,200 | B2 * | 10/2011 | Tearney et al. | 600/407 |
| 8,050,740 | B2 * | 11/2011 | Davis et al. | 600/430 |
| 2006/0276709 | A1 | 12/2006 | Khamene et al. | |
| 2012/0022381 | A1 * | 1/2012 | Tearney et al. | 600/479 |

FOREIGN PATENT DOCUMENTS

| WO | WO03011764 | 2/2003 |
|---|---|---|
| WO | WO2005051187 | 6/2005 |

OTHER PUBLICATIONS

Cassidy et al., "Molecular Imaging Perspectives", J.R. Soc. Interface, 2005, pp. 1-12.
Yang et al., "2 PI Ambiguity-Free Optical Distance Measurement with Subnanometer Prevision with a Novel Phase-Crossing Low-Coherence Interferometer", Optics Letters 27, 77-79 (2002).

(Continued)

*Primary Examiner* — Unsu Jung
*Assistant Examiner* — Amanda Lauritzen

(57) ABSTRACT

A localization system to localize an interventional instrument in the body of a patient. The localization system includes an electromagnetic wave source which splits an electromagnetic signal into components propagating along a probe path and a reference path, respectively. The probe path includes a signal outlet for emitting the signal at the point to be located and at least one detector for picking up the emitted signal. A correlator is used to determine the correlation between the signal components that propagated along the probe path and the reference path respectively. Knowing the length of the reference path, the unknown distance between the signal outlet and the detector in the probe path can be estimated based on the correlation information.

10 Claims, 1 Drawing Sheet

OTHER PUBLICATIONS

Fercher et al., "Eye Length Measurement by Interferometry with Partially Coherent Light", Optics Letters 13, 186-188 (1988).

Huang et al., "Optical Coherence Tomography", Science, vol. 254, No. 5035, 1178-1181, 1991.

* cited by examiner

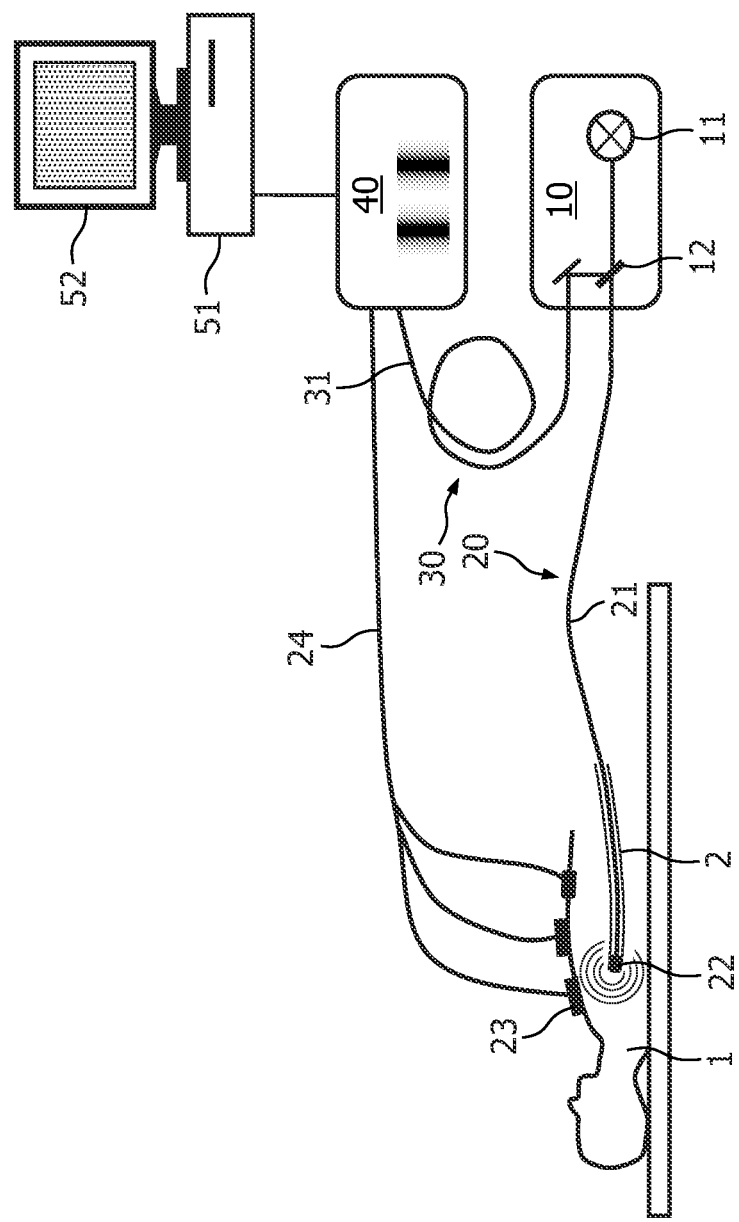

ELECTROMAGNETIC LOCALIZATION SYSTEM

CROSS REFERENCE TO RELATED CASES

This application claims the benefit and is a National Stage of International Application Number PCT/IB2008/051541, filed Apr. 22, 2008, and claims the benefit of Provisional Application Ser. No. 60/914,049, filed Apr. 26, 2007.

The invention relates to a localization system and a method for localizing a point of interest, particularly an interventional instrument. Moreover, it relates to a medical system comprising such a localization system, as well as to a computer program and a record carrier related to said method.

Today many diagnostic and therapeutic procedures are done by minimal invasive interventions to reduce the costs and the risks for the patient. A typical example of such interventions is the navigation of a catheter in the vessel system of a patient. The U.S. Pat. No. 7,152,608 B2 describes in this respect a localization system comprising external magnetic field generators and a sensor probe attached to a catheter which is inserted into the body of a patient. By sensing the magnitude of the externally generated magnetic fields, the sensor can infer its own spatial position and thus localize the catheter within the body.

Based on this background it was an object of the present invention to provide alternative means for the localization of interventional instruments, wherein it is desired that these means are cost effective in an everyday clinical use and/or robust with respect to their measurement results.

This object is achieved by a localization system according to claim 1, a medical system according to claim 7, a method according to claim 8, a computer program according to claim 9, and a record carrier according to claim 10. Preferred embodiments are disclosed in the dependent claims.

The localization system according to the present invention serves for the localization of a point of interest, for example the tip of a surgical instrument like a catheter, an endoscope, or a needle, during its navigation through the body of a patient. The localization system comprises the following components:

a) An electromagnetic wave source for generating an electromagnetic signal and for splitting this into components that propagate in parallel along at least one probe path and along a reference path. The electromagnetic wave source is preferably a microwave source providing an electromagnetic signal with a frequency in the range of typically about 1 kHz to 100 GHz.

b) The aforementioned at least one probe path, wherein this probe path comprises:

A signal outlet for emitting at a spatial point of interest the electromagnetic signal component that propagates along the probe path. The signal outlet may for example be the end of a waveguide that is located at the tip of a catheter which shall be tracked. The electromagnetic signal is typically radiated from the signal outlet in many directions, preferably even isotropically in all directions.

A detector for picking up the aforementioned electromagnetic signal component that was emitted at the signal outlet. The "picking up" of the signal component shall comprise in this context the collection of at least a part of the signal component's energy, such that the form (and information) of the signal is preserved. As the electromagnetic wave will typically spread from the signal outlet in many directions, the detector will in fact usually capture only a small fraction of the emitted energy.

c) A correlator for determining the correlation between the electromagnetic signal components that propagated along the probe path and the reference path, respectively. Optically such a correlation corresponds to the interference of the signal components from the probe and the reference path, i.e. the correlator can be realized by an optical interferometer.

d) An evaluation unit for estimating the spatial location of the signal outlet—and thus of the point of interest—from the aforementioned determined correlation between signal components of the probe and the reference path. In this context, the "estimation of the location" of the signal outlet shall in a broad sense mean any restriction of the possible whereabouts of the signal outlet. By determining the distance between the signal outlet and a detector, the whereabouts of the signal outlet can for example be restricted to lie (anywhere) on a sphere around the detector. Preferably, the signal outlet is localized with no remaining degree of freedom or uncertainty, i.e. at a particular point in space.

The evaluation unit may for example be realized by dedicated electronic hardware and/or a digital data processing unit with appropriate software.

The proposed localization system compares the components of an electromagnetic signal that propagated along a probe path and along a reference path, respectively, wherein a maximal correlation indicates that the probe path and the reference path have equal (optical) lengths. Knowing the length of the reference path will therefore allow to infer the length of the probe path and thus of the unknown distance between signal outlet and detector that is part of the probe path. An advantage of this method with respect to optical tracking systems is that it works without a visual contact between the signal outlet and the detector. An advantage with respect to magnetic tracking systems is that the method is not sensitive to disturbances due to external magnetic or electrical fields or due to the presence of e.g. magnetic materials.

In a preferred embodiment of the invention, the localization system comprises at least two, preferably at least three probe paths that share the signal outlet but have individual detectors disposed at different positions in space. Thus the different probe paths have an identical first section extending from the electromagnetic wave source to the signal outlet, and individual second sections extending from the signal outlet to one particular detector for each probe path and further from said detector to the correlator. In other words, a single strand of probe paths splits into a plurality of branches at the signal outlet. As was already explained, the correlation between the electromagnetic signal components in a probe path and in the reference path can be used to eliminate one degree of freedom with respect to the possible whereabouts of the signal outlet. Using two detectors (with known relative or absolute positions in space), the location of the signal outlet can therefore be restricted to a one-dimensional line in space, which may sometimes be sufficient for the user. Using three detector allows in principle to eliminate all three degrees of freedom and thus to localize the signal outlet at a definite point in space. More than three detectors can favorably be used to increase the accuracy of the localization by providing additional data for error correction procedures and for resolving possible ambiguities in the data of three detectors.

The detector that is used in the at least one probe path is preferably sensitive in all spatial directions and therefore capable to fully measure each three-dimensional polarization vector of an incident electromagnetic field. This can for example be achieved by a system of three mutually orthogonal dipoles each of which is sensitive to the polarization in one spatial direction. The complete measurement of the three-dimensional polarization vector of the electromagnetic signal component propagating in the probe path guarantees that no signal energy is lost irrespective of the orientation of the detector. Moreover, it allows to infer the spatial direction in which the signal outlet lies relative to the corresponding detector and thus provides additional information that can be exploited for the localization of the signal outlet.

The overall accuracy of the localization system depends crucially on the precision with which the correlation between the electromagnetic signal components in the probe path and the reference path can be determined, particularly on the precision with which the maximum of the correlation (i.e. an equal length of probe path and reference path) can be detected. In this context it is preferred that the electromagnetic wave source is a low-coherence wave source, or, in other words, a wave source generating electromagnetic signals of a broad band width. In typical examples, the band width of the emitted electromagnetic signals ranges from 10 kHz to 10 GHz.

A low coherence of the emitted electromagnetic signals means that there is only a correspondingly small window around the exact equality of probe and reference path lengths in which a strong correlation occurs. Thus the equality of these lengths can be detected with high precision. Moreover, the broad band width has the advantage that the electromagnetic signal comprises with a high probability always frequencies that are not or only minimally attenuated by the material between the signal outlet and the detector.

In principle it is possible to dispose the signal outlet immediately at the electromagnetic wave source and/or to arrange the detector immediately at the correlator. In a preferred embodiment of the probe path, there is however a waveguide connecting the electromagnetic wave source with the signal outlet and/or a waveguide connecting the detector with the correlator. Similarly, the reference path may optionally comprise a waveguide. Typically, the reference path will completely lie within this waveguide that connects the electromagnetic wave source with the correlator. Due to the use of waveguides, the components of the localization system can be disposed at optimally suited positions in the workspace, for example at the tip of a catheter (signal outlet), on the skin of a patient (detectors), or at a convenient place for large apparatuses in the laboratory (wave source, correlator, evaluation unit). As the optical lengths of the wave guides are known and do not change, their incorporation implies no uncertainty with respect to the length of the probe path or reference path.

In a further development of the invention, the localization system comprises a tracking device for tracking the spatial position and/or orientation of the detector (or of the several detectors if there is a plurality of probe paths). This tracking device may be of any known design and apply any known measurement principle. It may particularly be an optical positioning system that determines the position of the detector according to stereoscopic principles from three or more camera pictures.

The invention further relates to a medical system comprising an interventional instrument, particular a catheter, an endoscope, or a needle, and further comprising a localization system of the kind described above, wherein the signal outlet of that localization system is attached to the instrument. If the instrument is a catheter, it could for example comprise a wave guide along which the electromagnetic signal component of the probe path propagates to the tip of the catheter where said wave guide has a signal outlet from which the electromagnetic signal is radiated into the surrounding tissue. The one or more detectors of the localization system may in this case be devices that can be attached to the skin of a patient.

The invention further relates to a method for localizing a point of interest in space, comprising the following steps:
a) The splitting of an electromagnetic signal into components propagating along at least one probe path and along a reference path, respectively.
b) In the at least one probe path:
   the emission of the electromagnetic signal component of the probe path from a signal outlet located at the point of interest;
   the picking up of the emitted electromagnetic signal component with a detector.
c) The determination of the correlation between the electromagnetic signal components that propagated along the probe path and the reference path, respectively.
d) The estimation of the location of the signal outlet relative to the detector based on the determined correlation.

The method comprises in general form the steps that can be executed with a localization system of the kind described above. Therefore, reference is made to the preceding description for more information on the details, advantages and improvements of that method.

The invention further relates to a computer program enabling the execution of steps c) and/or d) of a method of the kind described above, i.e. for the determination of the correlation between electromagnetic signal components that propagated along a probe path and a reference path, respectively, and/or for the estimation of the location of a signal outlet relative to a detector based on said determined correlation, wherein the signal outlet and the detector are successive stations in the probe path.

Finally, the invention comprises a record carrier, for example a floppy disk, a hard disk, or a compact disc (CD), on which a computer program of the aforementioned kind is stored.

These and other aspects of the invention will be apparent from and elucidated with reference to the embodiment(s) described hereinafter. These embodiments will be described by way of example with the help of the accompanying single drawing which shows schematically a localization system according to the present invention.

Though the localization system is illustrated with respect to a medical application, particularly the navigation of a catheter 2 through the vessel system of a patient 1, the invention is not restricted to this area.

Existing mechanical, optical and magnetic device tracking technologies suffer from significant limitations. Mechanical tracking systems rigidly affix tools to a static reference frame (e.g. the operating table) using a series of joints that allow the tool to be manipulated. This approach is only appropriate for rigid tools and can significantly restrict range of motion/ ergonomics. Optical tracking systems, which attach light-emitting or reflecting markers to the interventional tools and use cameras to triangulate the tool's position, are also only appropriate for rigid tools and require an uninterrupted line-of-sight to be maintained between the markers and the cameras. Magnetic tracking systems use alternating magnetic fields to induce currents in sensor coils. This technology does not require a line-of-sight, and can be used to track non-rigid devices, but its accuracy is substantially worse than optical tracking methods and it has trouble working in the vicinity of metal objects, which distort magnetic fields.

In view of these problems, a novel approach to intra-procedural medical device tracking is proposed here, which offers substantial, clinically important, improvements relative to the existing technology. A localization system according to this proposal is illustrated as follows:

FIGURE includes a low-coherence electromagnetic wave source with a wave generator that generates an electromagnetic signal with predefined spectral characteristics containing frequencies that can be successfully transmitted through biological tissue in accordance with an embodiment of the present system.

A low-coherence (wide bandwidth) electromagnetic wave source 10 with a wave generator 11 (e.g. LED or halogen lamp) that generates an electromagnetic signal with predefined spectral characteristics containing frequencies that can be successfully transmitted through biological tissue (i.e. frequencies for which tissue appears at least partially transparent). This electromagnetic signal is divided by a beam splitter 12 into two components that will propagate along a "probe path 20" and a "reference path 30", respectively, wherein the reference path has a known path length.

In the aforementioned probe path 20, the system comprises:
A first wide-bandwidth wave guide 21 that starts at the wave source 10, runs along a cardiac catheter 2 through the body of the patient 1, and ends at the tip of the catheter 2.
A signal outlet 22 at the distal end of the first wave guide 21, from which the signal component of the probe path is radiated into the surrounding blood/tissue.
A number of skin-based radiation detectors 23, each with the capability of detecting the polarization vector of the received signal, i.e. of the signal component of the probe path emitted at the signal outlet 22. The detectors 23 optionally include three-axis orthogonal polarization sensitive detectors (e.g. three orthogonal dipoles). The amplitude and phase measurements of signals received by each dipole then provides necessary information for an accurate determination of the relative angle of the transmitter radiator (dipole) angle and every skin-based detector.
A number of second wide-bandwidth wave guides 24 that guide the signal component picked up by the detectors 23 to an interferometer 40.

In the reference path 30, the system comprises
a third wide-bandwidth wave guide 31 that starts at the wave source 10 and ends at the interferometer 40.

The localization system further comprises:
The mentioned interferometer 40 that serves as a correlator and processes the optical signals of the probe path and the reference path, respectively, which come in via the second and third wave guides 24 and 31.
A PC 51 or workstation that uses the interferometry measurements to calculate the 3D position/orientation of the catheter 2 with high temporal and spatial resolution and optionally represents them on an intra-procedural display 52.

An essential component of the system is the correlator or interferometer 40. Interferometry refers to the process of combining signals with a wave structure in such a way that the waves "interfere" with each other by combining destructively and/or constructively. The result is an interference pattern that potentially contains useful quantitative information. Low-coherence interferometry is a technique that involves using a wave source with low temporal coherence, such as white light, to generate two signals; one signal is used as a reference signal and the other signal is used as a "probe" (cf. Yang, C. H., Wax, A., Dasari, R. R., Feld, M. S.: "2 pi ambiguity-free optical distance measurement with subnanometer precision with a novel phase-crossing low-coherence interferometer", Optics Letters 27, 77-79 (2002)). The two signals are then re-combined and the resulting interference pattern, due to slight phase and/or amplitude alterations experienced by the probe signal, enables quantitative measurements to be performed. One application of low-coherence interferometry in the medical domain is an imaging technique called optical coherence tomography OCT (cf. AF. Fercher, K. Mengedoht, W. Werner: "Eye length measurement by interferometry with partially coherent light", Optics Letters 13, 186-188 (1988); D. Huang, E. A. Swanson, C. P. Lin, et al.: "Optical Coherence Tomography", Science, vol. 254, no. 5035, pp. 1178-1181, 1991; WO2003011764A2).

The same principle that allows OCT to measure the depth of anatomical boundaries (i.e. anatomical features that reflect some of the optical probe signal) is used by the proposed localization system to measure the position of medical devices during a minimally invasive interventional procedure. As shown in the example of the FIGURE, the electromagnetic "probe signal" component is routed to this end through the device (here the catheter 2) using electromagnetic waveguides (21) and radiated from the device's tip; it is collected by electromagnetic detectors (23) on the patient's skin and routed back to an interferometer (40) where it is combined with the reference signal component, which was routed directly from the source (10) along a waveguide (31) with a known length. The interference pattern in the interferometer then provides information about the relative difference in path length that was traversed by the probe and reference signal components; this type of measurement from multiple detectors on the patient's skin will enable the position of the device to be calculated with an axial spatial resolution proportional to the electromagnetic signal bandwidth.

Since the tip of a device like the catheter 2 can be tracked inside the patient's body, the described technique is appropriate for non-rigid tools (e.g. catheters, endoscopes, and flexible needles). And since there is no line-of-sight requirement or rigid attachment to a static reference frame, the proposed technology does not negatively impact workflow or restrict range of motion. Additionally, the low-coherence electromagnetic signal enables the non-linear electrical properties of biologic tissue and/or the interventional environment to be characterized and corrected for. The interferometry-based measurements (device position and orientation) can be performed with extremely high spatial resolution.

A calibration technique may be applied to establish the relative positions and angular inclinations of the skin-based detectors 23, which must be known to the PC 51 to allow the desired triangulation of the catheter 2. The calibration technique could use pre- or intra-procedural imaging, e.g. fluoroscopy, Computed Tomography (CT), Magnetic Resonance Imaging (MRI), or the like. Alternatively, it could use a standard (e.g. optical) tracking device to measure the positions of the skin-based detectors 23.

Optionally, a technique to correct for differences in tissue properties (i.e. electrical permittivity) may be applied to optimize tracking accuracy.

The following mathematical algorithm, implemented in a software application that will run on the PC 51, can be used analyze the measurements of the interferometer 40 and to solve the relative position and angular inclination of the intra-procedural device 2 relative to the body-based sensors 23. The algorithm uses the definition of coherence as the average Fourier transform of the normalized cross-correlation:

$$S_{xy}(f) = \int_{-\infty}^{\infty} r_{xy}(\tau) e^{-j2\pi f \tau} d\tau$$

$$c_{xy} = \frac{1}{(f_{max} - f_{min})} \int_{f_{min}}^{f_{max}} S_{xy}(f) df$$

$$r_{xy}(\tau) = \int_{-\infty}^{\infty} \bar{x}(\tau) y(t+\tau) d\tau$$

where $S_{xy}(f)$ is the power spectral density of the cross correlation $r_{xy}(\tau)$ of the signals (interfered signals), and $c_{xy}$ is the coherence coefficient for signals x and y, and $f_{max}$, $f_{min}$ are the maximum and minimum frequencies of the signal, respectively. A "low coherence signal" assumes a high value for the expression $(f_{max} - f_{min})$.

Finding the relative position of the signal outlet 22 with respect to a detector 23 is equivalent to finding the value ti that maximizes the power spectral density $S_{xy}(f)$ for any $f \in [f_{max} - f_n]$. As indicated above, this task will be assumed by the supporting software running on the local PC.

It should be noted that the axial spatial resolution $\Delta x/x$ of the measurement is given by $$\frac{\Delta x}{x} = l_c = \frac{2\ln 2}{\pi} \frac{\lambda_0^2}{\Delta\lambda} = \frac{2\ln 2}{\pi} \frac{\lambda_0^2}{c}(f_{max} - f_{min})$$

where $\lambda_0^2$ is the central wavelength of the injected electromagnetic signal and $\Delta\lambda$ is the total wavelength dispersion of the same.

The described evaluation of the measurements requires the following modules:

An FFT algorithm capable of processing the cross correlation data.

A simplex algorithm required for maximizing the spectral power density determined for each interferer.

An amplitude and phase estimator for every polarization orientation of the receivers (dipoles) within every body-based sensor 23.

An algorithm to process the above in order to determine the angular inclination of the catheter to every body-based sensor.

The proposed tracking technology provides functionality that is critical for enabling and improving minimally invasive interventional procedures, e.g. catheter-based cardiovascular procedures and needle-based biopsy/ablation procedures. The primary capability provided by intra-procedural device tracking is the ability to augment and optimize the intra-procedural visualization of medical image data. The most appropriate image slice/volume can be automatically selected based on the current position of the interventional device, and the image data can be augmented with graphics that clearly indicate, in real-time, the position of the interventional tools relative to anatomical structures of interest. Active device tracking also enables intra-procedural image acquisition to be optimized (e.g. scan plane and image acquisition parameters can be updated based on the current device position/motion). Moreover, tracking the position and motion of internal devices enables physiologic motion (i.e. cardiac and respiratory motion) to be characterized and compensated for.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A localization system comprising
    an electromagnetic wave source for splitting an electromagnetic signal into components and propagating the components along at least one probe path and along a reference path;
    a signal outlet attached to an end of the at least one probe path for emitting the electromagnetic signal component propagating the probe path, the end is positioned at a point of interest;
    a detector for picking up the emitted electromagnetic signal component from the signal outlet;
    a correlator for correlating the electromagnetic signal components propagated long the probe path and the reference path; and
    an evaluation unit for estimating a spatial location of the signal outlet relative to the detector based on the correlation.

2. The localization system according to claim 1, further comprising at least two probe paths that share the signal outlet, each having individual detectors disposed at different positions.

3. The localization system according to claim 1, wherein the detector sensitive in all spatial directions.

4. The localization system according to claim 1, wherein the electromagnetic wave source is a low-coherence wave source.

5. The localization system according to claim 1, further comprising at least one waveguide for connecting the electromagnetic wave source with the signal outlet the detector with the correlator and/or the electromagnetic wave source with the correlator.

6. The localization system according to claim 1, further comprising a tracking device for tracking the spatial position and/or orientation of the detector.

7. The localization system according to claim 1, further comprising an interventional instrument selected from one of a catheter, an endoscope, and a needle, wherein the signal outlet is attached to the instrument.

8. A method for localizing a point of interest, the method comprising acts of:
    splitting an electromagnetic signal into components;
    propagating the components along at least one probe path and along a reference path;
    emitting the electromagnetic signal component propagating the probe path from a signal outlet attached to an end of the at least one probe path, the end is located at the point of interest;
    picking up the emitted electromagnetic signal component with a detector from the signal outlet;
    a processor correlating the electromagnetic signal components propagated along the probe path and the reference path; and
    the processor estimating a spatial location of the signal outlet relative to the detector based on the correlation.

9. The method according to claim 8, wherein the acts of correlating and estimating are performed by the processor running a computer program.

10. A non-transitory computer readable record carrier on which a computer program is stored that when executed by a processor the computer program performing acts comprising;
    splitting an electromagnetic signal into components;
    propagating the components along at least one probe path and along reference path;

emitting the electromagnetic signal component propagating the probe path from signal outlet attached to an end of the at least one probe path, the end is located at the point of interest;
picking up the emitted electromagnetic signal component with a detector from the signal outlet;
correlating the electromagnetic signal components propagated along the probe path and the reference path; and
estimating a spatial location of the signal outlet relative to the detector based on the correlation.

* * * * *